United States Patent
Yang et al.

(10) Patent No.: US 10,151,723 B2
(45) Date of Patent: Dec. 11, 2018

(54) PARTICULATE MATTER SENSOR AND MEASUREMENT METHOD THEREOF

(71) Applicant: Hyundai Motor Company, Seoul (KR)

(72) Inventors: Sang Hyeok Yang, Gyeonggi-do (KR); Dong Gu Kim, Gyeonggi-do (KR)

(73) Assignee: Hyundai Motor Company, Seoul (KR)

( * ) Notice: Subject to any disclaimer, the term of this patent is extended or adjusted under 35 U.S.C. 154(b) by 172 days.

(21) Appl. No.: 15/187,323

(22) Filed: Jun. 20, 2016

(65) Prior Publication Data

US 2017/0168002 A1 Jun. 15, 2017

(30) Foreign Application Priority Data

Dec. 11, 2015 (KR) .................. 10-2015-0177466

(51) Int. Cl.
*G01N 27/24* (2006.01)
*F01N 11/00* (2006.01)
(Continued)

(52) U.S. Cl.
CPC ............. *G01N 27/24* (2013.01); *F01N 11/00* (2013.01); *G01N 15/0606* (2013.01);
(Continued)

(58) Field of Classification Search
CPC ........... G01N 15/0656; G01N 27/4071; G01N 15/0606; G01N 2015/0046; G01N 15/06; G01N 27/4067
See application file for complete search history.

(56) References Cited

U.S. PATENT DOCUMENTS 4,294,679 A * 10/1981 Maurer .............. G01N 27/4067 204/426
4,300,990 A * 11/1981 Maurer .............. G01N 27/4071 204/412
(Continued)

FOREIGN PATENT DOCUMENTS

EP 1925926 A1 * 5/2008 ......... G01N 15/0656
JP 2010054432 A * 3/2010 ......... G01N 27/4071
(Continued)

OTHER PUBLICATIONS

Machine translation of EP 1925926 A1, originally published on May 2008.*
(Continued)

*Primary Examiner* — David A Rogers
(74) *Attorney, Agent, or Firm* — Mintz Levin Cohn Ferris Glovsky and Popeo, P.C.; Peter F. Corless

(57) ABSTRACT

A particulate matter sensor is disposed in an exhaust line of an exhaust system, and configured to sense particulate matter included in exhaust gas. The particulate matter sensor includes: a first substrate, a second substrate, and a third substrate stacked sequentially from a bottom to form a sensing unit at one end part and a signal processor at another end part. The sensing unit includes: a reference electrode formed on one surface of the first substrate and having a constant capacitance value; a temperature sensor formed on one surface of the second substrate and sensing a temperature and a heater electrode disposed to be adjacent to the temperature sensor; and a main electrode formed on one surface of the third substrate and having a capacitance value that is varied by the particulate matter.

3 Claims, 3 Drawing Sheets

(51) Int. Cl.
  *G01N 27/22* (2006.01)
  *G01N 15/06* (2006.01)
  *G01N 15/00* (2006.01)
(52) U.S. Cl.
  CPC ....... *G01N 15/0656* (2013.01); *G01N 27/226* (2013.01); *F01N 2560/05* (2013.01); *F01N 2560/06* (2013.01); *F01N 2560/20* (2013.01); *G01N 2015/0046* (2013.01)

(56) References Cited

U.S. PATENT DOCUMENTS

| | | | | |
|---|---|---|---|---|
| 5,236,569 | A * | 8/1993 | Murase | G01N 27/417 204/410 |
| 5,922,946 | A * | 7/1999 | Hirota | F16N 29/00 73/61.71 |
| 6,136,170 | A * | 10/2000 | Inoue | G01N 27/4065 204/408 |
| 6,634,210 | B1 * | 10/2003 | Bosch | G01N 15/0656 204/426 |
| 7,275,415 | B2 * | 10/2007 | Rhodes | F01N 11/00 73/28.01 |
| 7,280,028 | B2 * | 10/2007 | Nelson | G01K 7/18 338/22 R |
| 7,534,032 | B2 * | 5/2009 | Reithofer | D06M 15/3562 219/448.11 |
| 7,543,477 | B2 * | 6/2009 | Berger | G01N 15/0656 73/23.33 |
| 7,574,895 | B2 * | 8/2009 | Schnell | G01N 15/0656 73/28.01 |
| 7,609,068 | B2 * | 10/2009 | Ripley | G01N 15/0656 324/500 |
| 7,770,432 | B2 * | 8/2010 | Roesch | G01N 15/0656 73/23.33 |
| 7,862,649 | B2 * | 1/2011 | Sakuma | G01N 15/0656 55/282.3 |
| 7,872,466 | B2 * | 1/2011 | Dorfmueller | G01N 15/0656 324/515 |
| 7,886,578 | B2 * | 2/2011 | Schmidt | G01N 15/0656 73/28.01 |
| 8,176,768 | B2 * | 5/2012 | Kondo | G01N 15/0656 73/23.33 |
| 8,225,640 | B2 * | 7/2012 | Nelson | G01N 15/0656 73/28.01 |
| 8,230,716 | B2 * | 7/2012 | Nelson | F02D 41/1466 324/693 |
| 8,249,827 | B2 * | 8/2012 | Nelson | F02D 41/1466 324/71.1 |
| 8,377,274 | B2 * | 2/2013 | Ohya | G01N 27/4075 204/421 |
| 8,578,756 | B2 * | 11/2013 | Suzuki | G01K 7/16 73/23.31 |
| 8,635,900 | B2 * | 1/2014 | Ante | F02D 41/1466 73/23.33 |
| 8,736,284 | B2 | 5/2014 | Aoki | |
| 8,788,184 | B2 * | 7/2014 | Baumann | F01N 11/00 123/697 |
| 8,794,046 | B2 * | 8/2014 | Roesch | F02D 41/222 73/1.01 |
| 8,823,400 | B2 * | 9/2014 | Hocken | F02D 41/1466 324/691 |
| 8,823,401 | B2 * | 9/2014 | Roth | G01N 15/0656 324/699 |
| 8,860,439 | B2 * | 10/2014 | Kimata | F01N 11/00 324/464 |
| 8,915,645 | B2 * | 12/2014 | Genssle | F01N 11/002 374/1 |
| 8,928,338 | B2 * | 1/2015 | Nelson | F02D 41/1466 324/464 |
| 9,134,216 | B2 * | 9/2015 | Hedayat | G01N 15/0656 |
| 9,316,574 | B2 * | 4/2016 | Sakamoto | G01N 15/0656 |
| 9,334,773 | B2 * | 5/2016 | Lin | F01N 3/023 |
| 9,389,163 | B2 * | 7/2016 | Hedayat | G01N 15/0656 |
| 9,528,971 | B2 * | 12/2016 | Teranishi | G01N 33/0047 |
| 9,535,027 | B2 * | 1/2017 | Feldman | G01N 27/327 |
| 2001/0035044 | A1 * | 11/2001 | Larsson | G01N 1/2202 73/28.01 |
| 2001/0051108 | A1 * | 12/2001 | Schonauer | G01N 25/22 422/68.1 |
| 2002/0036138 | A1 * | 3/2002 | Kuroki | G01N 27/4071 204/426 |
| 2004/0149595 | A1 * | 8/2004 | Moore | F01N 3/28 205/784.5 |
| 2006/0016687 | A1 * | 1/2006 | Wallace | G01N 27/4071 204/515 |
| 2006/0151338 | A1 * | 7/2006 | Wang | G01N 27/4071 205/780.5 |
| 2008/0190173 | A1 * | 8/2008 | Wienand | G01N 15/0656 73/28.01 |
| 2009/0051376 | A1 * | 2/2009 | Schnell | G01N 15/0656 324/724 |
| 2009/0056416 | A1 * | 3/2009 | Nair | G01N 15/0656 73/28.01 |
| 2009/0090622 | A1 * | 4/2009 | Ripley | G01N 15/0656 204/401 |
| 2009/0280240 | A1 * | 11/2009 | Ohya | G01N 27/4075 427/125 |
| 2010/0066388 | A1 * | 3/2010 | Wienand | G01N 15/0656 324/649 |
| 2010/0147052 | A1 * | 6/2010 | Nelson | G01N 15/0656 73/28.01 |
| 2011/0139618 | A1 * | 6/2011 | Serrels | G01N 27/4071 204/408 |
| 2011/0162439 | A1 * | 7/2011 | Ayliffe | B01L 3/502715 73/61.71 |
| 2011/0214988 | A1 * | 9/2011 | Yoshida | G01N 27/4175 204/406 |
| 2011/0314796 | A1 * | 12/2011 | Nakamura | F01N 9/002 60/276 |
| 2011/0320171 | A1 * | 12/2011 | Okayama | B01D 46/0086 702/183 |
| 2012/0261067 | A1 * | 10/2012 | Ayliffe | B01L 3/502707 156/277 |
| 2012/0266646 | A1 * | 10/2012 | Maeda | F02D 41/1466 73/1.06 |
| 2014/0034495 | A1 * | 2/2014 | Grass | G01N 27/419 204/408 |
| 2014/0116113 | A1 * | 5/2014 | Lee | G01N 15/0656 73/28.01 |
| 2014/0345362 | A1 * | 11/2014 | Lee | G01N 15/0656 73/23.31 |
| 2015/0177204 | A1 * | 6/2015 | Bessen | G01N 15/0656 73/1.06 |
| 2015/0192545 | A1 * | 7/2015 | Sugiyama | G01N 27/70 73/28.01 |
| 2016/0017830 | A1 * | 1/2016 | Wienand | G01N 15/0656 73/23.31 |
| 2016/0054256 | A1 * | 2/2016 | Sakuma | G01N 27/4071 204/408 |
| 2016/0097752 | A1 * | 4/2016 | Weber | G01K 7/16 73/1.06 |

FOREIGN PATENT DOCUMENTS

| | | |
|---|---|---|
| JP | 2013-174448 A | 9/2013 |
| JP | 5288472 B2 | 9/2013 |
| JP | 5331578 B2 | 10/2013 |
| JP | 2014-041034 A | 3/2014 |
| JP | 5561262 B2 | 7/2014 |
| KR | 10-1243645 B1 | 3/2013 |

OTHER PUBLICATIONS

Machine translation of JP 2010054432 A, originally published on Mar. 2010.*

* cited by examiner

PARTICULATE MATTER SENSOR AND MEASUREMENT METHOD THEREOF

CROSS-REFERENCE TO RELATED APPLICATION

This application claims under 35 U.S.C. § 119(a) the benefit of Korean Patent Application No. 10-2015-0177466 filed in the Korean Intellectual Property Office on Dec. 11, 2015, the entire contents of which are incorporated herein by reference.

BACKGROUND (a) Field of the Invention

The present invention relates to a particulate matter sensor and a measuring method thereof, and more particularly, to a particulate matter sensor that compares a capacitance value of a reference electrode, which is constantly maintained, and a capacitance value of a main electrode, which is varied by particulate matter so as to strongly correspond to external noise and environmental changes.

(b) Description of the Related Art

Recently, as exhaust gas regulations of vehicles have been strengthened, attention to a post-processing apparatus for purifying exhaust gas has increased.

Particularly, as a diesel engine vehicle generates an exhaust flow including particulate matter (PM) of a varying amount, the diesel engine vehicle is known to be a major cause of air pollution such that regulations thereof are becoming more stringent.

To reduce the particulate matter of the diesel vehicle, a diesel particulate filter (DPF) is applied to the exhaust gas, and a particulate matter sensor is used to sense an amount of particulate trapped in the diesel particulate filter.

The particulate matter sensor detects changes of resistance or capacitance generated as the particulate matter included in the exhaust is accumulated, and is installed at the rear end of the diesel particulate filter in an exhaust system.

Methods of operating the particulate matter sensor may be classified into an accumulation method and a real-time method.

The particulate matter sensor of the accumulation method used in most vehicles senses a change of current flow as the particulate matter is accumulated on two digital electrodes applied with voltages.

The particulate matter sensor of the accumulation method has a simple structure such that its reliability is high and its manufacturing cost is low, thereby being appropriate for used in a vehicle.

However, an initial cumulative time is required until the change signal of the current flow is generated in the particulate matter sensor of the accumulation method.

On the other hand, in the particulate matter sensor of the real-time method, the amount of the particulate matter is monitored in real time by detecting an ionization reaction of the particulate matter.

However, the particulate matter sensor of the real time method has low accuracy and a size that is bulky such that it is difficult to be downsized.

Accordingly, research on a particulate matter sensor that accurately and rapidly measures the particulate matter in the exhaust gas of the exhaust system is required.

The above information disclosed in this Background section is only for enhancement of understanding of the background of the invention and therefore it may contain information that does not form the prior art that is already known in this country to a person of ordinary skill in the art.

SUMMARY

An exemplary embodiment of the present invention provides a particulate matter sensor and a measuring method using the same that accurately and rapidly measures the particulate matter in an external environment by comparing a capacitance value of a reference electrode, which is constantly maintained, and a capacitance value of a main electrode, which is varied by particulate matter.

A particulate matter sensor is disposed in an exhaust line of an exhaust system and configured to sense particulate matter included in exhaust gas. The particulate matter sensor includes: a first substrate, a second substrate, and a third substrate stacked sequentially from a bottom to form a sensing unit at one end part and a signal processor at another other end part, wherein the sensing unit includes: a reference electrode formed on one surface of the first substrate and having a constant capacitance value; a temperature sensor formed on one surface of the second substrate and sensing a temperature and a heater electrode disposed to be adjacent to the temperature sensor; and a main electrode formed on one surface of the third substrate and having a capacitance value that is varied by the particulate matter.

The signal processor may output a difference between the constant capacitance value of the reference electrode and the varied capacitance value of the main electrode.

The main electrode may further include an insulating layer enclosing an upper part thereof.

The temperature sensor may be formed to enclose an exterior surface of the heater electrode.

The temperature sensor and the heater electrode may be formed at the same distance from the reference electrode and the main electrode between the reference electrode and the main electrode.

The heater electrode may burn the particulate matter accumulated on the insulating layer formed on the main electrode to remove it.

The first substrate may be formed with a thicker thickness than the second substrate and the third substrate.

The first substrate to the third substrate may be formed of one of a ceramic substrate and a silicon substrate.

A method for measuring particulate matter may include steps of: measuring a first capacitance value through a reference electrode; measuring a second capacitance value through a main electrode; receiving the first capacitance value and the second capacitance value through a signal processor; and generating a final output voltage by using the first capacitance value and the second capacitance value input to the signal processor.

In an exemplary embodiment of the present invention, by applying the reference electrode that constantly maintains its capacitance value, the sensing accuracy may be improved.

That is, by using the difference between the output voltages generated by the constantly maintained capacitance value of the reference electrode and the capacitance value of the main electrode that is varied by the particulate matter, sensing may be accurately performed in all environments.

Further, effects that can be obtained or expected from exemplary embodiments of the present invention are directly or suggestively described in the following detailed description. That is, various effects expected from exemplary embodiments of the present invention will be described in the following detailed description.

DETAILED DESCRIPTION OF THE EMBODIMENTS

Figure 1:
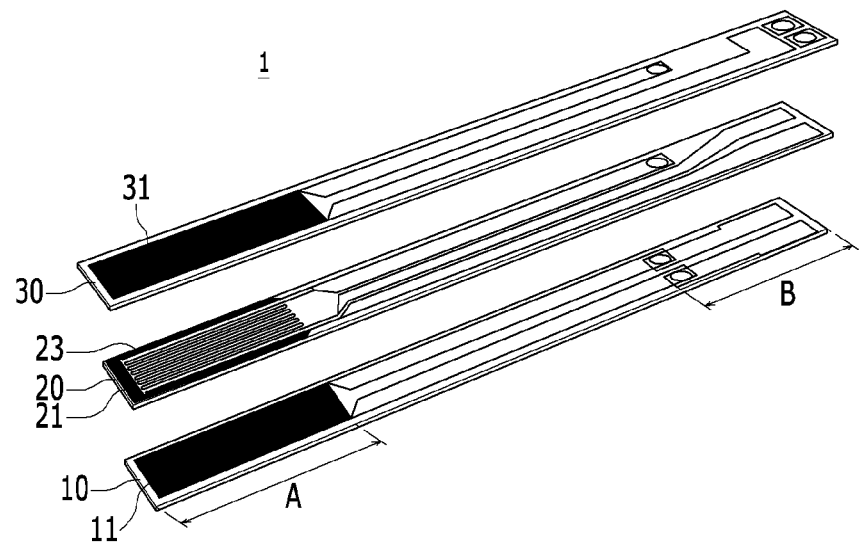
FIG. 1 is an exploded perspective view of a particulate matter sensor according to an exemplary embodiment of the present invention.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Throughout the specification, unless explicitly described to the contrary, the word "comprise" and variations such as "comprises" or "comprising" will be understood to imply the inclusion of stated elements but not the exclusion of any other elements. In addition, the terms "unit", "-er", "-or", and "module" described in the specification mean units for processing at least one function and operation, and can be implemented by hardware components or software components and combinations thereof.

Further, the control logic of the present invention may be embodied as non-transitory computer readable media on a computer readable medium containing executable program instructions executed by a processor, controller or the like. Examples of computer readable media include, but are not limited to, ROM, RAM, compact disc (CD)-ROMs, magnetic tapes, floppy disks, flash drives, smart cards and optical data storage devices. The computer readable medium can also be distributed in network coupled computer systems so that the computer readable media is stored and executed in a distributed fashion, e.g., by a telematics server or a Controller Area Network (CAN).

Hereinafter, exemplary embodiments of the present invention will be described with reference to the accompanying drawings. However, the drawings and a detailed description to be described later relate to an exemplary embodiment of several exemplary embodiments for effectively describing a characteristic of the present invention. Therefore, the present invention is not limited to only the following drawings and description.

Figure 2:
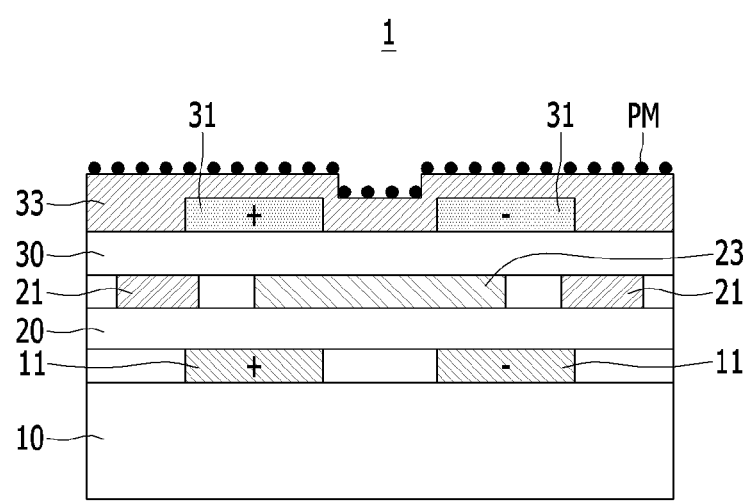
FIG. 2 is a cross-sectional view of one end part of a particulate matter sensor according to an exemplary embodiment of the present invention.

FIG. 1 is an exploded perspective view of a particulate matter sensor according to an exemplary embodiment of the present invention, and FIG. 2 is a cross-sectional view of one end part of a particulate matter sensor according to an exemplary embodiment of the present invention.

Exhaust gas flows in an exhaust line of a vehicle, and particulate matter is included in the exhaust gas.

A particulate matter sensor according to an exemplary embodiment of the present invention is disposed in the exhaust line to measure the particulate matter included in the exhaust gas.

Referring to FIGS. 1 and 2, the particulate matter sensor 1 is formed by stacking a plurality of substrates, a sensing unit A is formed in one end part of the substrate, and a signal processor B is formed in another end part (i.e., the opposite end part) of the substrate.

Here, the plurality of substrates includes a first substrate 10, a second substrate 20, and a third substrate 30, and preferably are made of one of a ceramic substrate and a silicon substrate.

The sensing unit A preferably includes a reference electrode 11, a temperature sensor 21, a heater electrode 23, and a main electrode 31.

The reference electrode 11 is formed on one surface of the first substrate 10 and has a constant capacitance value.

In this case, the first substrate 10 is formed to a sufficient thickness such that particulate matter PM deposited on the other surface of the first substrate 10 does not affect the reference electrode 11.

That is, the first substrate 10 is formed thickly such that the particulate matter PM deposited on the other surface of the first substrate 10 is prevented from affecting a capacitance value of the reference electrode 11.

The first substrate 10 is formed thicker than the second substrate 20 and the third substrate 30, however it is not limited thereto, and the thicknesses of the first substrate 10, the second substrate 20, and the third substrate 30 may be changed if necessary.

The temperature sensor 21 is formed on one surface of the second substrate 20 to sense a surrounding temperature.

The heater electrode 23 is patterned to be adjacent to the temperature sensor 21 on one surface of the second substrate 20, and is made of a metal material.

In this case, the metal material may be made of at least one of Pt, Mo, and W.

The heater electrode 23 serves to burn the particulate matter PM accumulated on an insulating layer 33 on the main electrode 31, as described later, in order to remove it.

The temperature sensor 21 is formed with a shape enclosing the exterior surface of the heater electrode 23, however it is not limited thereto, and the shape of the temperature sensor 21 and the heater electrode 23 may be changed.

The temperature sensor 21 and the heater electrode 23 having this configuration may be formed at the same layer and the distance between the reference electrode 11, and the temperature sensor 21 and the heater electrode 23 may be the same as the distance between the main electrode 31, and the temperature sensor 21 and the heater electrode 23.

That is, the second substrate 20 formed with the temperature sensor 21 and the heater electrode 23 and the third substrate 30 formed with the main electrode 31 positioned on the temperature sensor 21 and the heater electrode 23 are formed with the same thickness.

This is to apply the same temperature condition to the reference electrode 11 and the main electrode 31 as the heater electrode 23 is positioned at the same distance from the reference electrode 11 and the main electrode 31.

In an exemplary embodiment of the present invention, the temperature sensor 21 and the heater electrode 23 are formed at the same layer in one substrate, however it is not limited thereto, and the temperature sensor 21 may be formed in a different substrate from the heater electrode 23.

The main electrode 31 is formed on one surface of the third substrate 30 such that the capacitance value is varied by the particulate matter PM.

The insulating layer 33 made of a thin film is formed on the main electrode 31.

In this case, the insulating layer 33 covers the main electrode 31 to insulate positive and negative poles of the main electrode 31 that are adjacent to each other.

The particulate matter PM is deposited on the insulating layer 33, and the particulate matter PM is easily removed by heat generated by the heater electrode 23.

Further, the signal processor B may use a signal processing circuit of a general particulate matter sensor.

The signal processor B is electrically connected to the reference electrode 11, the temperature sensor 21, the heater electrode 23, and the main electrode 31.

For example, the signal processor B is electrically connected to the reference electrode 11, the temperature sensor 21, the heater electrode 23, and the main electrode 31 through wires.

The signal processor B outputs a difference between the constant capacitance value of the reference electrode 11 and the varied capacitance value of the main electrode 31.

Figure 3:
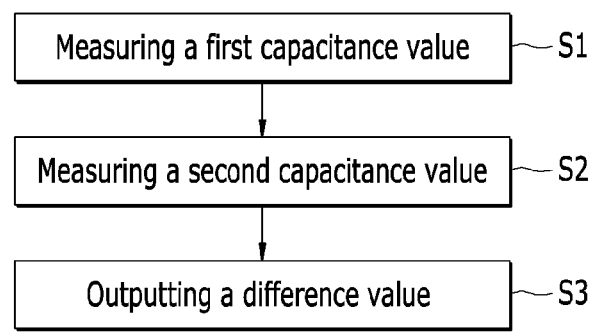
FIG. 3 is a flowchart of a measuring method of a particulate matter sensor according to an exemplary embodiment of the present invention.

FIG. 3 is a flowchart of a measuring method of a particulate matter sensor according to an exemplary embodiment of the present invention.

The particulate matter PM included in the exhaust gas in the exhaust system of the vehicle is accumulated to the insulating layer 33 on the main electrode 31 while passing through the particulate matter sensor 1 according to an exemplary embodiment of the present invention.

Accordingly, as the particulate matter PM is accumulated, the capacitance value is changed by the charge induced to the main electrode 31.

Referring to FIG. 3, a step (S1) of measuring the first capacitance value through the reference electrode 11 is performed.

In this case, the first capacitance value is a value representing a capacitance change of the reference electrode 11, and since the capacitance change of the reference electrode 11 is extremely small, the value is approximately 0.

Next, a step (S2) of measuring the second capacitance value through the main electrode 31 is performed.

In this case, the second capacitance value is a value that is varied as the particulate matter PM is accumulated to the insulating layer 33 on the main substrate 31.

Subsequently, the signal processor B receives the first capacitance value and the second capacitance value.

Next, a step (S3) of generating a final output voltage by using the first capacitance value and the second capacitance value that are input to the signal processor B is performed.

In addition, the signal processor B receives the capacitance value that is changed by the surrounding environment, that is, mechanical, electronic, and temperature changes, etc.

That is, the signal processor B receives the capacitance value that is changed by the noise of the surrounding environment.

Also, in the signal processor B, a capacitance value that is fixed to generate the final output voltage is predetermined.

In this case, in the step (S3) of generating the final output voltage, a step in which the signal processor B generates the first output voltage by the first capacitance value is performed.

In this case, the first output voltage may be calculated by [Equation 1].

$$V_{O1} = V_I * \frac{C_{IN1} + C_T}{C0} \qquad \text{[Equation 1]}$$

Here, $V_{O1}$ represents the first output voltage, $V_I$ represents an application voltage, $C_{IN1}$ represents the first capacitance change value, $C_T$ represents the value that is changed by the surrounding environment, that is, the capacitance value due to the noise, and C0 may be the capacitance value that is previously input to the signal processor and is fixed to generate the final output voltage.

In this case, the application voltage may be an application voltage applied to the particulate matter sensor 1.

After generating the first output voltage, a step in which the signal processor B generates the second output voltage by the second capacitance value is performed.

In this case, the second output voltage may be calculated by [Equation 2].

$$V_{O2} = V_I * \frac{C_{IN2} + C_T}{C0} \qquad \text{[Equation 2]}$$

Here, $V_{O2}$ represents the second output voltage, $V_I$ represents the application voltage, $C_{IN2}$ represents the second capacitance change value, $C_T$ represents a value that is changed by the surrounding environment, that is, the capacitance value due to the noise, and C0 may be the capacitance value that is previously input to the signal processor and is fixed to generate the final output voltage.

In this case, the application voltage may be the application voltage applied to the particulate matter sensor 1.

Next, a step in which the signal processor B generates the final output voltage depending on the difference between the first output voltage and the second output voltage is performed.

In this case, the final output voltage may be calculated by [Equation 3].

$$V_F = V_{O1} - V_{O2} = V_I * \frac{C_{IN2} - C_{IN2}}{C0} \qquad \text{[Equation 3]}$$

Here, $V_F$ represents the final output voltage, $V_{O1}$ and $V_{O2}$ respectively represent the first output voltage and the second output voltage, $V_I$ represents the application voltage, $C_{IN2}$ and $C_{IN2}$ respectively represent the first capacitance change value and the second capacitance change value, and C0 may be the capacitance value that is previously input to the signal processor and is fixed to generate the final output voltage.

Accordingly, the final output voltage is calculated while removing $C_T$, which is a common noise that is added by the surrounding environment, such as the mechanical, electrical, and temperature change noise.

In this case, since the magnitude of $C_{IN1}$ representing the first capacitance change value of the reference electrode 11 is insignificant, if approximated, the value $C_{IN2}$ only representing the second capacitance change value of the main electrode 31 remains and is output.

Finally, a step of burning the particulate matter PM accumulated to the insulating layer 33 on the main electrode 31 to be removed through the heater electrode 23 positioned between the reference electrode 11 and the main electrode 31 is performed.

Accordingly, the particulate matter sensor 1 and the measuring method according to an exemplary embodiment of the present invention compares the first capacitance value of the reference electrode 11 and the second capacitance value of the main electrode 31 that is varied by the particulate matter PM to output the difference value, thereby strongly corresponding to external noise and environmental changes.

In addition, in the particulate matter sensor 1, the temperature sensor 21 and the heater electrode 23 are patterned together on one substrate, thereby simplifying the process.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A method for measuring particulate matter, comprising the steps of:

measuring a first capacitance value through a reference electrode;

measuring a second capacitance value through a main electrode;

receiving the first capacitance value and the second capacitance value through a signal processor; and generating a final output voltage by using the first capacitance value and the second capacitance value input to the signal processor, wherein the step of generating the final output voltage further comprises:

generating the first output voltage by using a first capacitance change value of the first capacitance value, a capacitance value due to noise, and an application voltage;

generating a second output voltage by using a second capacitance change value of the second capacitance value, the capacitance value due to noise, and the application voltage; and generating a final output voltage depending on a difference between the first output voltage and the second output voltage.

2. The method of claim 1, wherein in the step of measuring the second capacitance value through the main electrode, the second capacitance value is varied by the particulate matter accumulated to the insulating layer formed on the main electrode.

3. The method of claim 1, further comprising the step of:

burning the particulate matter accumulated on an insulating layer on the main electrode through a heater electrode positioned between the reference electrode and the main electrode.

* * * * *